(12) United States Patent
Lavallee et al.

(10) Patent No.: US 10,262,084 B2
(45) Date of Patent: Apr. 16, 2019

(54) METHOD FOR CONSTRUCTING A PATIENT-SPECIFIC SURGICAL GUIDE

(71) Applicant: ORTHOTAXY, La Tronche (FR)

(72) Inventors: Stéphane Lavallee, St Martin d'Uriage (FR); Guillaume Mersch, St Martin d'Heres (FR)

(73) Assignee: MINMAXMEDICAL, La Tronche (FR)

( * ) Notice: Subject to any disclaimer, the term of this patent is extended or adjusted under 35 U.S.C. 154(b) by 126 days.

(21) Appl. No.: 15/032,223

(22) PCT Filed: Nov. 7, 2014

(86) PCT No.: PCT/EP2014/074040
§ 371 (c)(1),
(2) Date: Apr. 26, 2016

(87) PCT Pub. No.: WO2015/067752
PCT Pub. Date: May 14, 2015

(65) Prior Publication Data
US 2016/0274571 A1 Sep. 22, 2016

(30) Foreign Application Priority Data
Nov. 8, 2013 (EP) .................................... 13306531

(51) Int. Cl.
*G06F 17/50* (2006.01)
*A61B 34/10* (2016.01)
(Continued)

(52) U.S. Cl.
CPC ............ *G06F 17/50* (2013.01); *A61B 17/155* (2013.01); *A61B 17/157* (2013.01);
(Continued)

(58) Field of Classification Search
CPC ...... G05B 19/4099; G05B 2219/49023; A61B 34/10; A61B 17/1764; A61B 17/155;
(Continued)

(56) References Cited

U.S. PATENT DOCUMENTS

| | | | |
|---|---|---|---|
| 2006/0142657 A1 | 6/2006 | Quaid et al. | |
| 2006/0195111 A1* | 8/2006 | Couture | A61B 17/15 606/86 R |

(Continued)

FOREIGN PATENT DOCUMENTS

WO    WO 9325157    12/1993

OTHER PUBLICATIONS

International Search Report and Written Opinion of the ISA in PCT/EP2014/74040 dated Feb. 6, 2015. 8 pages.
(Continued)

*Primary Examiner* — Ajay Ojha
(74) *Attorney, Agent, or Firm* — Womble Bond Dickinson (US) LLP

(57) ABSTRACT

The invention relates to a method for constructing a patient-specific surgical guide comprising at least one contact element comprising a contact surface intended to match an anatomical structure to be treated and at least one guiding element for guiding a surgical instrument to treat said anatomical structure, said method comprising: —receiving a 3D medical image of the anatomical structure of the patient; —determining, in said 3D medical image, at least one region of interest containing a portion of the external surface of the anatomical structure intended to match a respective contact element of the surgical guide; —segmenting the 3D medical image in said determined region of interest so as to locally reconstruct the external surface of the anatomical structure; —computing the contact surface of the contact element from said reconstructed local surface of the anatomical structure;
(Continued)

—constructing the at least one contact element to include the contact surface. —defining the position of the at least one guiding element with respect to the anatomical structure; —constructing the surgical guide by generating a rigid body including the at least one guiding element and said at least one contact element.

15 Claims, 4 Drawing Sheets

(51) Int. Cl.
    *A61B 17/15*      (2006.01)
    *A61B 17/17*      (2006.01)
    *G05B 19/4099*      (2006.01)
    *A61B 17/56*      (2006.01)

(52) U.S. Cl.
    CPC .......... *A61B 17/1764* (2013.01); *A61B 34/10* (2016.02); *G05B 19/4099* (2013.01); *A61B 2017/568* (2013.01); *A61B 2034/108* (2016.02); *G05B 2219/49023* (2013.01)

(58) Field of Classification Search
    CPC ............ A61B 17/157; A61B 2034/108; A61B 2017/568; A61B 2219/49023
    See application file for complete search history.

(56) References Cited

U.S. PATENT DOCUMENTS

| 2007/0103464 A1* | 5/2007 | Kaufman | G06T 7/0012 345/424 |
| 2008/0065084 A1* | 3/2008 | Couture | A61B 17/154 606/281 |
| 2008/0119712 A1 | 5/2008 | Lloyd | |
| 2011/0282473 A1 | 11/2011 | Pavlovskaia et al. | |
| 2013/0166256 A1 | 6/2013 | Wirx-Speetjens et al. | |
| 2013/0331844 A1* | 12/2013 | Booth | A61B 17/155 606/88 |

OTHER PUBLICATIONS

Search Report in European Application No. 13306531.8 dated Jan. 28, 2014. 5 pages.

* cited by examiner

METHOD FOR CONSTRUCTING A PATIENT-SPECIFIC SURGICAL GUIDE

FIELD OF THE INVENTION

The invention relates to a method for constructing a patient-specific surgical guide comprising at least one contact element intended to match an anatomical structure to be treated and at least one guiding element for guiding a surgical instrument to treat said anatomical structure.

BACKGROUND OF THE INVENTION

Patient-specific surgical guides become more and more used in dentistry or orthopedic surgery, for example in view of implanting total knee prosthesis.

A patient-specific guide is generated by an additive manufacturing technique (e.g. stereolithography) by including two kinds of elements:
contact elements intended to match an anatomical structure (e.g. a bone) to be treated; and
guiding elements such as drill guides, saw guides, or milling guides, intended to guide a surgical instrument to carry out the desired treatment once the patient-specific guide is positioned onto the anatomical structure of the patient. The planning of the position of the guiding elements corresponds to the planning of the intended treatment of the anatomical structure.

The contact elements are chosen so as to provide a unique and stable position of the guide with respect to the anatomical structure.

FIG. 1 is a schematic view of an example of a patient-specific guide 1 positioned onto a patient's anatomical structure 2.

The guide 1 comprises a contact element 11 having a surface in contact with the anatomical structure 2, a guiding element 12 for a saw blade and a guiding element 13 for a drill.

WO 93/25157 describes a method for constructing a patient-specific surgical guide.

A 3D medical image (e.g. CT or MRI) of an anatomical structure of the patient is first segmented so as to reconstruct the anatomical structure, i.e. to form a 3D model of the anatomical structure. Such a 3D model is a representation of the 3D surface of the anatomical structure (for example using triangular facets) or a representation of the volume of the anatomical structure (for example using voxels) which implicitly defines its surface.

Then, contact points and/or contact faces are defined on the surface of the reconstructed anatomical structure so as to provide unique and stable positioning of the guide.

On the other hand, the position of the guiding elements with respect to the anatomical structure is defined.

Then, the surgical guide is constructed by generating a rigid body including the guiding elements and the contact elements. By "rigid" is meant here that the guide is not intended to deform during the surgical intervention.

The surgical guide can then be produced by an additive manufacturing technique.

Such a method is long and expensive for the following reasons.

In practice, it involves several flows of data between a radiologist who has acquired the 3D medical image, an expert center that carries out the segmentation of the 3D medical image and the planning of the surgical guides, and the surgeon who has ordered the patient-specific guide.

Typically, at least four flows of data and/or material are to be considered in such a process:

(A) The 3D medical image is sent by the radiologist to the expert center that carries out a segmentation of the 3D medical image so as to reconstruct the anatomical structure and determines a planning comprising a proposed position of the guiding elements.

The expert center usually comprises experts (engineers and/or technicians) in the processing of medical images.

The experts use specific tools for facilitating the segmentation of the images.

However, since the 3D medical image usually comprises a plurality of slices—typically from 150 to 200 slices—an error in the segmentation of only one slice may generate a large error in the final result.

Hence, the segmentation cannot be completely carried out automatically, and the expert has to segment manually at least the regions of the 3D medical image where the greyscale impedes an automatic recognition of the pixels between bone and soft tissues.

Such a manual segmentation is time-consuming (sometimes several hours) and increases the cost of the surgical guide.

The planning is usually based on standard default parameters.

(B) The expert center sends the planning to the surgeon.

(C) The surgeon checks and, if necessary, modifies the planning.

However, depending on the format of the planning data provided by the expert center, it may be difficult and unpractical for the surgeon to modify the planning.

Hence, the surgeon may be incited to accept the planning as provided by the expert who is usually not a surgeon; this situation is not satisfactory in terms of involvement of the surgeon in the planning step and more specifically in terms of responsibility.

(D) Based on the planning and the segmented image, the expert center constructs the surgical guide.

Said construction typically relies on the subtraction of the volume of a body comprising the guiding elements and intersecting the anatomical structure on the one hand, and of the volume of the anatomical structure.

Then, the expert center manufactures the guide (or orders it to a dedicated manufacturing center) and sends it to the surgeon.

Although such a patient-specific guide strongly reduces the time spent in the operating room and drastically reduces the instrumentation required for carrying out the surgical intervention, many surgeons report that they have some difficulties in accurately positioning the guide onto the anatomical structure.

A slight mismatch between the surface of the contact element of the guide and the respective surface of the anatomical structure may result in an angular error of several degrees in the orientation of the guiding elements.

Such a mismatch may be caused by an inaccurate segmentation of the 3D medical image (in particular in osteophytes) or by soft tissues.

BRIEF DESCRIPTION OF THE INVENTION

A goal of the invention is to provide a method for constructing a patient-specific surgical guide that overcomes the drawbacks of the existing solutions.

In particular, this method should be less expensive and time-consuming as known methods, while improving the accuracy of the definition of the contact elements.

To that end, the invention provides a method for constructing a patient-specific surgical guide comprising at least one contact element comprising a contact surface intended to match an anatomical structure to be treated and at least one guiding element for guiding a surgical instrument to treat said anatomical structure, said method comprising:

receiving a 3D medical image of the anatomical structure of the patient;

determining, in said 3D medical image, at least one region of interest containing a portion of the external surface of the anatomical structure intended to match a respective contact element of the surgical guide;

segmenting the 3D medical image in said determined region of interest so as to locally reconstruct the external surface of the anatomical structure;

computing the contact surface of the contact element from said reconstructed local surface of the anatomical structure;

constructing the at least one contact element to include the contact surface.

defining the position of the at least one guiding element with respect to the anatomical structure;

constructing the surgical guide by generating a rigid body including the at least one guiding element and said at least one contact element.

By "anatomical structure" is meant in the present text a substantially rigid structure, such as a bone or cartilage, whose shape can be determined on medical images and whose shape will not substantially evolve between the acquisition of the medical images and the use of the guide. It can be but is not limited to an osseous structure.

By requiring only local segmentation of the 3D medical image (i.e. the segmentation between limited to the determined region(s) of interest), the construction of the guide is much quicker than conventional methods.

In addition, since the segmentation is limited to small regions of the image, one can afford a better accuracy of this operation.

Besides, said method provides a deeper involvement of the user in the construction of the guide, which is also beneficial to the accuracy of the guide.

According to an embodiment, the determination of the at least one region of interest is carried out automatically.

Advantageously, said at least one determined region of interest may further adjusted interactively by a user.

According to an embodiment, the automatic determination of the at least one region of interest is based on anatomical landmarks.

According to an embodiment, the automatic determination of the at least one region of interest is based on a prior rough segmentation of the 3D medical image.

According to an embodiment, the determination of the at least one region of interest is carried out interactively.

According to an embodiment, at least two separate regions of interest are determined in the 3D image, each region of interest containing a portion of the external surface of the anatomical structure intended to match a respective contact element of the surgical guide.

The construction of the contact element may then comprise extruding a part of the rigid body until the computed contact surface.

Preferably, the extrusion of said part of the rigid body is carried out by casting rays according to a selected direction towards the computed contact surface.

According to an advantageous embodiment, the contact surface is computed as an offset, by a determined distance along a direction opposite to the one of the rays, of the reconstructed local surface of the anatomical structure.

Alternatively, the computation of the contact surface may comprise, for each ray intersecting the reconstructed local surface of the anatomical structure at an intersection point, raising each intersection point to the highest of its neighbors, the contact surface being defined by said raised points.

According to an embodiment, the contact surface is computed as being the reconstructed local surface of the anatomical structure.

The construction of the contact element may comprise extruding a part of the rigid body toward the anatomical structure and subtracting the anatomical structure from said extruded part until the computed contact surface.

The guide can then be defined as an addition of at least two elements, wherein at least one element has at least one determined degree of freedom with respect to the anatomical structure.

Another aspect of the invention is a computer program product comprising computer-readable instructions which, when loaded and executed on a suitable system, perform the steps of the method described above.

BRIEF DESCRIPTION OF THE DRAWINGS

Other features and advantages of the invention will be apparent from the appended drawings, wherein.

DETAILED DESCRIPTION OF EMBODIMENTS OF THE INVENTION

Figure 1:
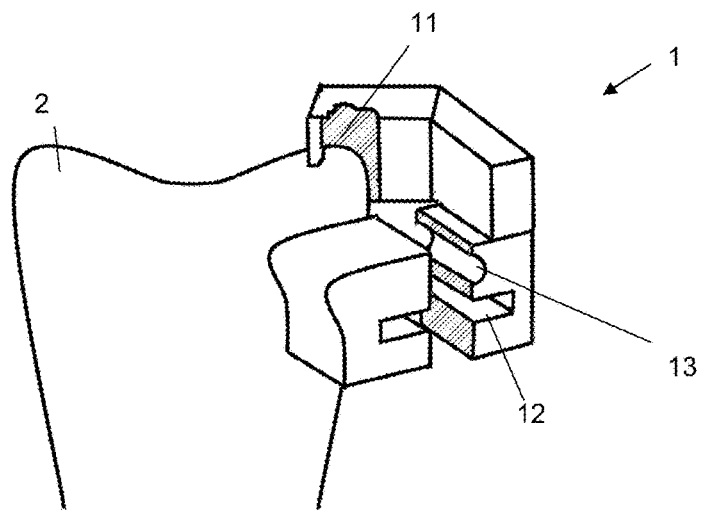
FIG. 1 is a schematic view of a patient-specific guide positioned onto a patient's anatomical structure.

The 3D medical image of the anatomical structure of the patient is acquired in a preliminary step that is not specifically included in the method according to the invention.

In this respect, said 3D medical image may be acquired at any time before carrying out this method, by any suitable technique such as Computed Tomography (CT) or Magnetic Resonance Imaging (MRI).

The method can be carried out by a computer system comprising at least one processor that is able to carry out the treatment of the 3D medical image and the construction of the elements of the guide. The system may also comprise a display device, such as a screen, for displaying the 3D image so as to allow the user to select the region(s) of interest, if appropriate, and/or for visualizing the different elements of the guide during the construction of the guide.

Determination of at Least One Region of Interest

In the method according to the invention, one or more regions of interest are defined in the 3D medical image.

Said one or more regions of interest are preferably placed on uneven areas of the anatomical structure of the patient. This relief is used to maximize guide stability and to make the guide positioning on the anatomical structure of the patient as univocal/easy as possible for the surgeon.

As an example, for the tibia, regions of interest can be preferably placed on the pre-spinal area and/or on the anterior edges of the tibial plateaus. For the femur, regions of interest can be preferably placed on the lateral edge of the lateral distal condyle and/or on the medial edge of the medial distal condyle.

Said one or more regions of interest can be automatically determined, for example based on: the position of some anatomical landmarks; a first rough automated segmentation; and/or the position of other elements of the patient-specific guide.

In a preferred embodiment, it is assumed that a user has previously selected some anatomical landmarks on a bone (we take the instance of a femur), using interactive and/or automated methods: femoral head center (H), knee center (K), most distal internal condyle (DI), most distal external condyle (DE), a point on the anterior cortex where the most proximal part of a femoral implant is supposed to be set (A), most posterior internal condyle (PI), most posterior external condyle (PE), internal epicondyle (EI), external epicondyle (EE). It is proposed to create a region of interest using simple geometrical rules based on those landmarks. For example, a simple cubical region of interest that will generate an anterior contact element can be built around a point (C)=(A)+10 mm×(KH), with three axis made of (KH), (EI EE) and the product of vectors (KH) and (EI EE). Many more complex geometrical rules can be defined to create regions of interest. Then the user has always the possibility to adjust manually the region of interest.

In another preferred embodiment, the same landmarks on a femur are used to warp a generic model of a standard femur such that the landmarks on the patient and the landmarks on the generic model will match. Such warping can be represented by a non-rigid 3D deformation W of a volume into a volume. The generic model may include predefined regions of interest defined by points and vectors. The predefined regions of interest of the generic model are then inferred on the patient by transforming said points and vectors using the warping function W.

In another preferred embodiment, it is assumed that a user has previously performed the planning, which consists in this particular example in defining the complete position and orientation of the femoral implant with respect to the 3D image in which the anatomical structure is visible. In that case, a first level of information is that the regions of interest must be placed outside of the volume of the implant set on the 3D image because the goal is to create guiding slots to cut the planes on which the implant will lie. Moreover, it is important to position the regions of interest that will define the contact elements as close as possible to the implant, in order to minimize the invasiveness of the guide. Some landmarks and directions can be defined on the implant. Then some geometrical rules are applied to build several regions of interest from said landmarks and directions. As an example, a region of interest having a size of ten millimeters can be defined to have a center located at a distance of six millimeters from a landmark of the implant (that is for example located on its internal side, at the intersection of the anterior plane and the anterior chamfer plane of the implant), said region of interest having a preferred direction orthogonal to said anterior chamfer plane.

Advantages of said automatic determination of said one or more regions of interest include a reduced time to design, which allows obtaining cheaper guides.

In addition, automatic determination allows the technician to focus on what can really affect guide performance, i.e. performing or checking the segmentation in the local regions of interest.

According to an embodiment, the one or more regions of interest can be defined interactively, for example by displaying both the region of interest and the 3D medical image in the same view.

Methods for displaying 3D medical images are well known, and include volume rendering.

Figure 2:
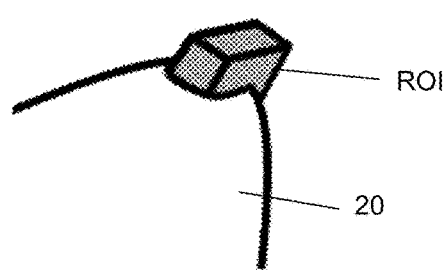
FIG. 2 is a schematic view showing the simultaneous display of a region of interest and of volume rendering of the anatomical structure.

FIG. 2 is a schematic view showing the simultaneous display of a region of interest (referred to as ROI) and of volume rendering 20 of the anatomical structure.

Another possible way of defining a region of interest interactively includes displaying one or more 2D slices of the 3D medical images in the region of interest.

In such case, it may be advantageous that said 2D slices of the 3D medical images in the region of interest are some of the slices on which the local reconstruction of the external surface of the anatomical structure will be subsequently performed.

Figure 3:
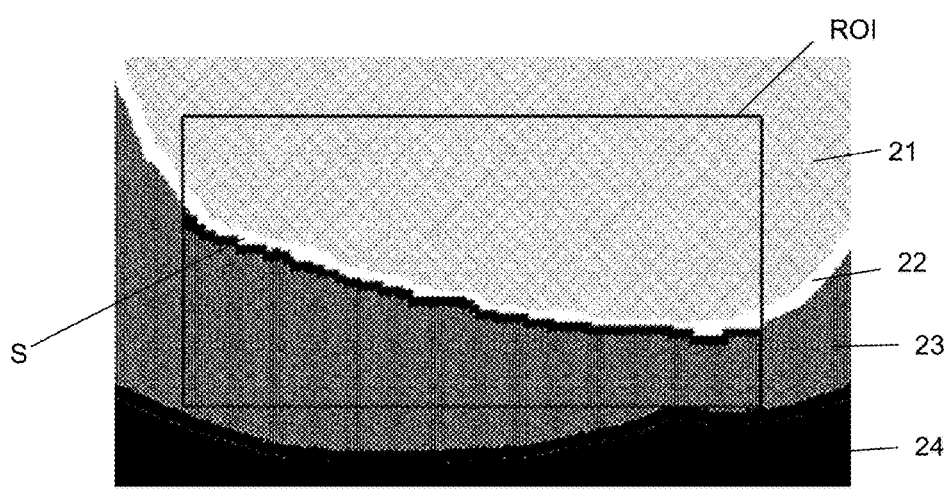
FIG. 3 is a schematic view of a local segmentation interface wherein the boundaries of the region of interest are displayed.

FIG. 3 is a schematic view of a local segmentation interface, wherein the boundaries of the region of interest ROI are displayed on a slice comprising different greyscale regions 21, 22, 23, 24. Region 21 corresponds to the anatomical structure and region 22 corresponds to the external surface of the anatomical structure, whereas regions 23 and 24 do not belong to the anatomical structure.

The 3D image is segmented inside said region of interest. The segmentation is represented by a surface S that is superimposed with the region 22.

In a preferred embodiment, 2D slices are reconstructed and displayed in the region of interest only. One can scroll the 3D image in this limited area only. A 2D slice appears as a small image with rows along a direction Y and columns along a direction X and the local segmentation process consists in selecting a curve that defines a function Y=f(X). So one wants to identify one pixel per vertical line. For that purpose, the user can click and drag the mouse to change the horizontal position of the points hovered by the mouse, which makes for very fast manual adjustments. Multiple other standard tools can be used for such semi-automated local segmentation (thresholding, spline interpolation, snakes, region growing, etc.). Typically, the curve obtained in one 2D slice serves as a basis for the next slice, and the process is repeated.

Because the ROI is relatively small, the edges of the anatomical structure inside the ROI have usually a similar appearance with respect to the surrounding soft tissues. Therefore, standard adaptive algorithms will have increased chances to be successful and offer fully automated and accurate segmentation. For example algorithms that search automatically for an optimal threshold that define the searched structure, with small variations from one area to the neighboring one can be extremely successful. There exists a very large number of automated segmentation methods of 2D and 3D images. For the vast majority of them, working in a small and relatively homogeneous sub-volume increases significantly their chances of success. A reasonable assumption is also to search for series of curves Y=f(X) as described above, which in 3D translates to the search of a function Z=f(X,Y), and this represents very useful priori information for automated segmentation algorithms (at the opposite of global segmentation methods that have very poor assumptions about the topology of the searched structure).

Moreover, because the ROI is small, the user can supervise the process of interactive or automated segmentation with a high degree of attention, which makes it safe.

Advantages of said interactive or automated determination of said one or more regions of interest include the fact that the definition of individual anatomy in a small area is made easier, faster and safer than a complete anatomical structure.

According to an embodiment, said one or more regions of interest can be automatically defined and further be fine-tuned interactively, which aggregates the advantages of automatic determination and interactive determination.

Local Reconstruction of the External Surface of the Anatomical Structure

After determination of the at least one region of interest, the 3D medical image is segmented in said determined region of interest so as to locally reconstruct the external surface of the anatomical structure.

This is a so-called local segmentation since the segmentation of the 3D image is carried out only in the determined region(s) of interest and no segmentation is carried out in the other regions of the 3D image.

Advantages of said local segmentation include a reduced time to perform and check segmentation since the amount of data to be treated is significantly reduced.

In addition, since the region(s) to be segmented are limited, the technician can focus on what can really affect guide performance, i.e. performing or checking the segmentation in the local regions of interest.

Besides, interactive reconstruction of the external surface of the anatomical structure is made easier. Indeed, very often and as illustrated in FIG. 3, the local external surface of the anatomical structure can be clearly determined in a single set of parallel images, with a sharp contrast between the anatomical structure (regions 21, 22) and its surroundings (regions 23, 24).

To the contrary, in view of a global segmentation of the 3D medical image, at least two different sets of parallel images are required.

Figure 4:
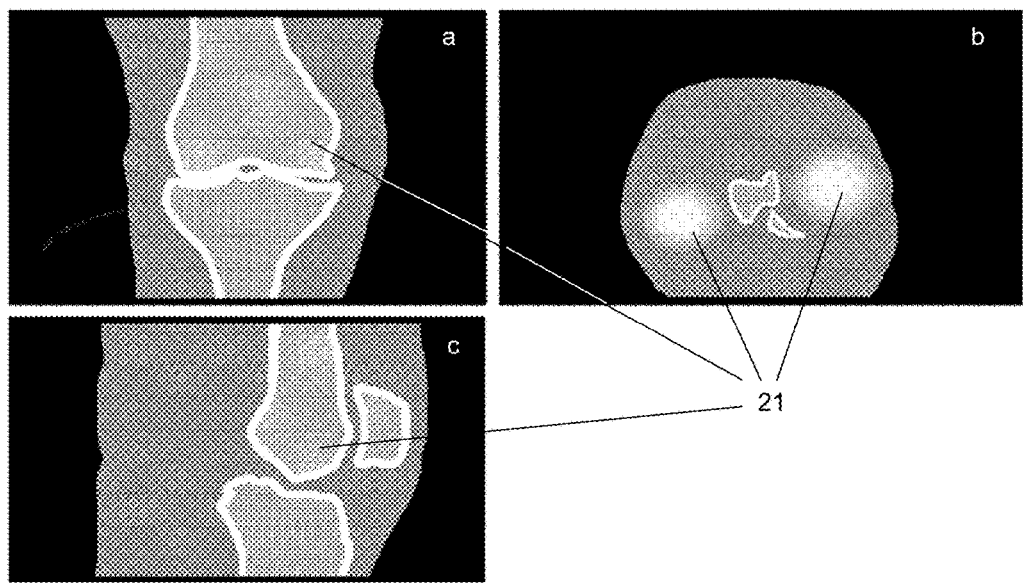
FIG. 4 is a schematic view showing different slices (a, b, c) of the 3D medical image to be used in case of a full segmentation of the anatomical structure.

FIG. 4 is a schematic view of different slices a, b, c of the 3D medical image showing the typical problem of full segmentation.

Slices such as slice b that is tangent to the anatomical structure 21 are blurry and the external surface of the anatomical structure is hard to select accurately in these slices, thus requiring a segmentation along the other directions.

FIG. 4 also shows that the segmentation is easier in slices such as slices a and c that are orthogonal to the external surface of the anatomical structure, where there can be a sharp contrast between the anatomical structure 21 and its surroundings.

Figure 5:
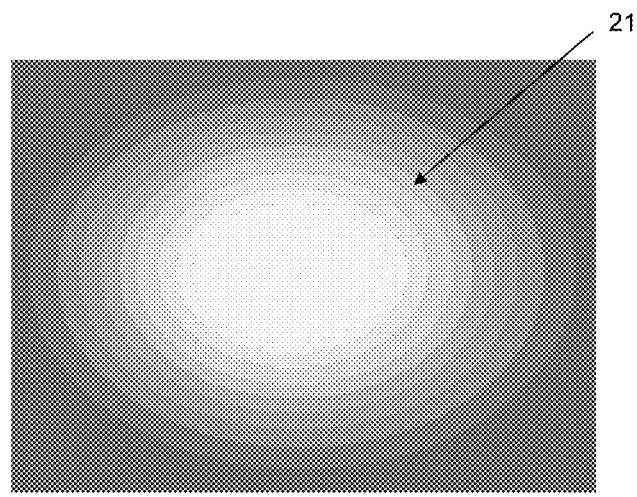
FIG. 5 is a zoom of FIG. 4b showing the graduated shading in the tangent plane of the external surface of the anatomical structure.

FIG. 5 is a zoom of slice b of FIG. 4 showing the graduated shading in the tangent plane of the external surface of the anatomical structure.

Another advantage of carrying out only a local segmentation is that automated reconstruction of the external surface of the anatomical structure is made easier. Indeed, very often, the range of values of the 3D medical images can vary greatly between different parts of the anatomical structure, e.g. cortical bone density is much higher than the density of bone on the femur distal condyles. In view of automatically computing an accurate global segmentation, advanced algorithms with adaptive thresholds would be required and usually fail. By contrast, since local segmentation involves only a limited part of the 3D image, it is less subjected to variation of the range of values and can thus be carried out by simpler algorithms.

Automated reconstruction of the external surface of the anatomical structure is also made easier on a selected slice of the 3D image. Indeed, as already explained above, the local external surface of the anatomical structure can be clearly determined in a single set of parallel images (such as slices a or c in FIG. 4), with a sharp contrast between the anatomical structure and its surroundings.

Automated reconstruction of the external surface of the anatomical structure is further rendered easier by the fact that, very often, the local external surface of the anatomical structure can be made to follow some general pattern on this single set of parallel images. This general pattern can generally be the same for all patients, which helps in making a robust algorithm. The segmentation can also generally be made to vary little between the slices, which further helps in making a robust algorithm.

Computation of the Contact Surface(s)

The contact surface on which the contact element of the patient-specific guide will be based can be the local reconstruction of the external surface of the anatomical structure.

However, it may be interesting to apply some transformations to said local reconstruction of the external surface of the anatomical structure.

Examples of said transformations include:

cropping, which sets on a given plane the local reconstruction which is on one side of the plane. It may prevent the patient-specific guide from being cut by a saw blade during surgery.

smoothing. It may reduce the size of the output and prevent sharp edges.

reduction of the number of surface descriptors (e.g. number of triangles or number of splines) without smoothing. It may reduce the size of the output.

offset, e.g. to adapt to some specific manufacturing machine, or to add some play where the assembly of the guide and the anatomical structure would otherwise be over-constrained.

other transformations, which may add some property to the guide, e.g. transformations which confer to the guide a preferred insertion direction with respect to a contact surface.

FIGS. 7 to 11 illustrate examples of such transformations.

Figure 7:
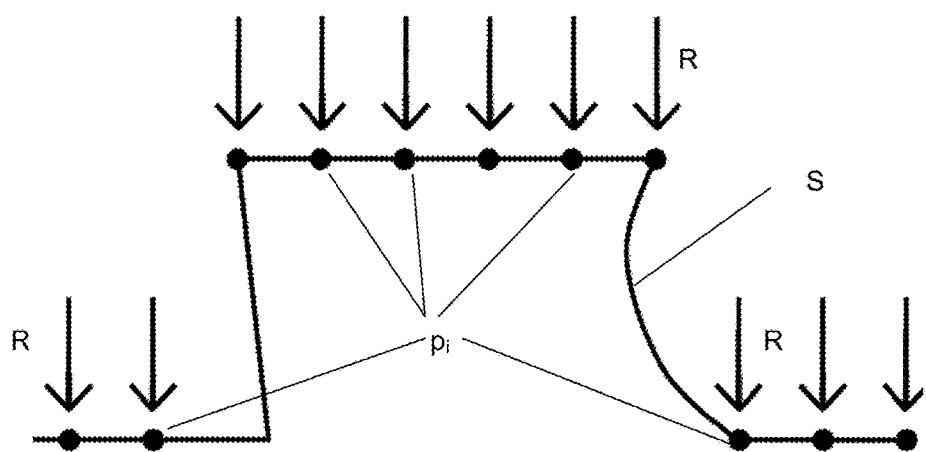
FIG. 7 shows raycasting onto the external surface of an anatomical structure with undercuts (or onto the reconstruction of the external surface of an anatomical structure with undercuts) to get a point cloud.
Figure 8:
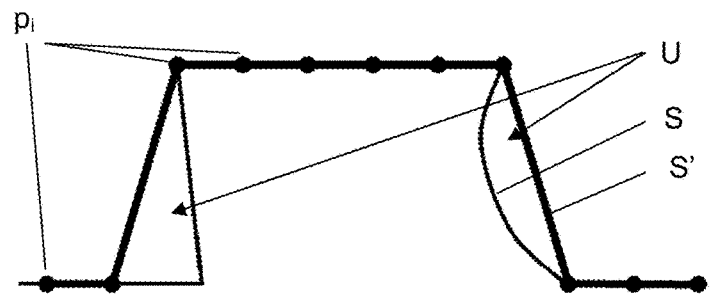
FIG. 8 shows how meshing the point cloud from FIG. 7 can remove undercuts.

According to an embodiment shown on FIGS. 7 and 8, the transformation comprises casting rays R in said preferred insertion direction towards said local reconstruction S of the external surface of the anatomical structure to compute their first intersection, which results in a point cloud formed of a plurality of points $p_i$ (FIG. 7); then meshing said point cloud so as to obtain a transformed surface S' (FIG. 8). Doing so is expected to remove most undercuts U before machining.

Figure 9:
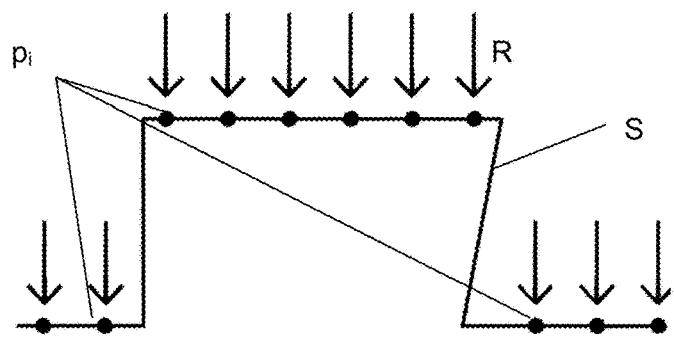
FIG. 9 shows raycasting onto the external surface of an anatomical structure with or without undercuts (or onto the reconstruction of the external surface of an anatomical structure with or without undercuts) to get a point cloud.
Figure 10:
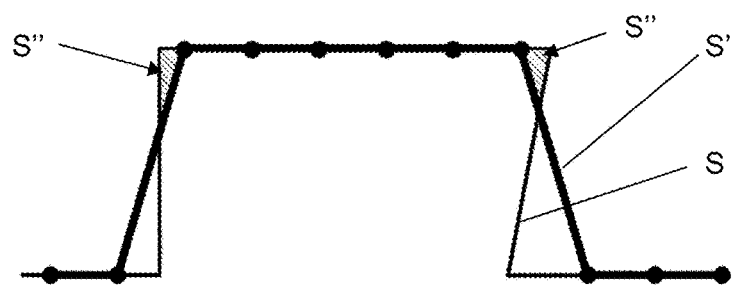
FIG. 10 shows how meshing the point cloud from FIG. 9 can result in a guide which is too tight to fit the anatomical structure.
Figure 11:
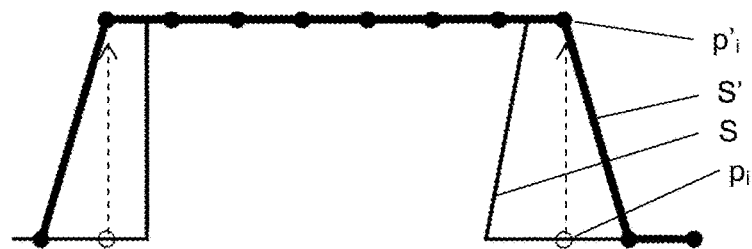
FIG. 11 shows how setting each point to the highest of its neighbors can effectively solve the issue of FIG. 10, resulting in a guide which will fit the anatomical structure.

However, in some cases, the guide may be too tight to fit the anatomical structure even without undercuts. Indeed, if the local reconstruction of the external surface has not been made in a sufficiently accurate way and/or if ray casting is thin enough, the point cloud may lack the points defining the extremities of a feature of the external surface of the anatomical structure (FIG. 9). As a consequence, the meshing of the point cloud may result in creating a surface S' that does not comprise undercuts but that however does not include portions S" of the surface S that do belong to the anatomical structure. Hence, the contact element that would be based on the surface S' would not fit the anatomical structure since it would interfere with the portions S".

According to an embodiment, the transformation comprises casting rays in said preferred insertion direction towards said local reconstruction S of the external surface of the anatomical structure to compute their first intersection, which results in a point cloud $p_i$; then raising each intersection point $p_i$ to the highest of its neighbors (represented by the dotted arrow in FIG. 11), which results in a second point cloud $p_i'$; then meshing said second point cloud. Said neighbors are not necessarily direct neighbors, they may also be neighbors in a fixed-distance vicinity, neighbors in a vicinity determined by the height gradient. Doing so is expected to further remove the undercuts before machining, even totally removing the undercuts (as compared to the situation of FIG. 10 meshing the point cloud from FIG. 9 can result in a guide which is too tight to fit the anatomical structure) if the step of the ray casting is thin enough and if the local reconstruction of the external surface of the anatomical structure is accurate.

According to an embodiment, the transformation comprises casting rays in said preferred insertion direction towards said local reconstruction of the external surface of the anatomical structure to compute their first intersection, which results in a point cloud; then raising each intersection point by a fixed offset, possibly negative, which results in a second point cloud$_i$; then meshing said second point cloud. Said neighbors are not necessarily direct neighbors, they may also be neighbors in a fixed-distance vicinity, neighbors in a vicinity determined by the height gradient. Doing so is expected to adapt the guide to the manufacturing installation and process.

Definition of the Contact Element(s)

As explained previously, the contact surface of the contact element is the reconstructed external surface of the anatomical structure (possibly after a transformation such as the ones described above).

Said contact surface is thus defined by a closed mesh.

According to an embodiment, the contact element may be computed by removing said closed mesh from uncut contact elements which intersect said closed mesh. Said uncut contact elements may be the whole patient-specific guide before removing the closed mesh. It is possible to do so in this method, by computing a closed mesh bounded by the contact surface on one side, and the region of interest on the other sides.

But Boolean operations on meshes are sometimes hard to implement.

To avoid said Boolean operations on meshes, it is possible, according to an alternative embodiment, to extrude a part of the rigid body forming the guide until the contact surface.

If appropriate, said extrusion may be made in the same direction as the cast rays used to compute the contact surface.

Definition of the Guiding Element(s)

Guiding elements have a shape that guides a surgical instrument, such as a slot to guide a saw blade, or a cylinder hole to guide a drill or a pin.

The construction of a guiding element usually involves digging a shape into a rigid body, but it can sometimes also involve the addition of matter to the guide, for example so that the drill bumps into a mechanical stop.

Construction of the Guide

The guide is defined as the sum of the guiding elements, the contact elements, and possibly some other elements such as junctions.

Guiding elements can also be contact elements (i.e. a single element may fulfill both contact and guiding functions), and it is possible to consider only one element which is the whole guide.

A preferred construction of the guide comprises an element-by-element construction of the guide, wherein each contact or guiding element is automatically placed and sized so that mechanical properties (e.g. stiffness), planning properties (e.g. position and orientation of a cutting plane, or position and orientation of a drill) and integrity of the guide (e.g. the final design must be printed as one single element) are fulfilled.

Figure 6:
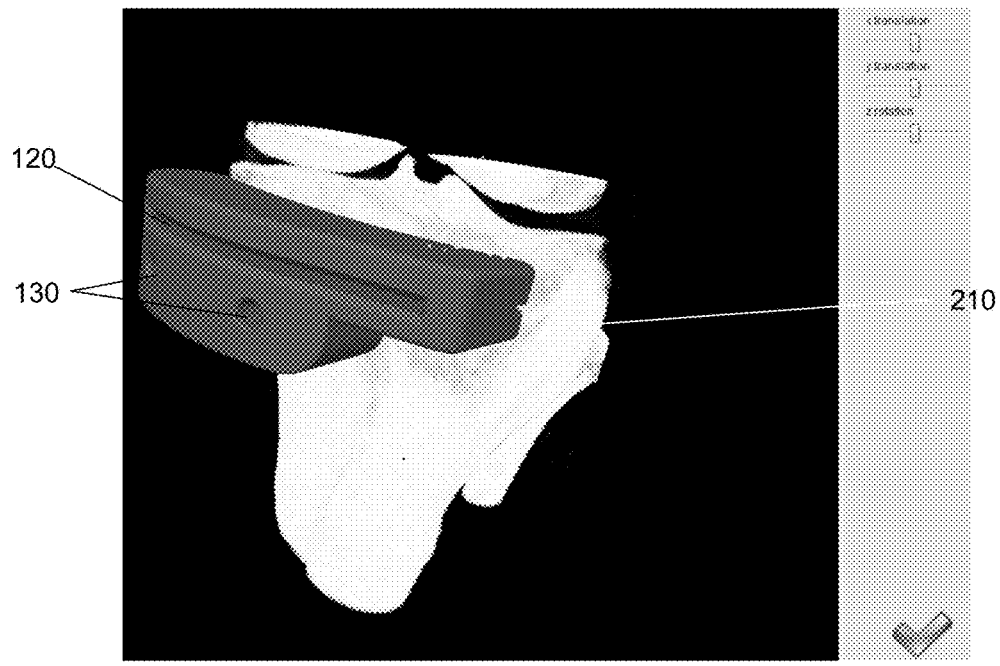
FIG. 6 is a possible display of an interface which places the guide elements one after another, in which the element is automatically placed (for example to stick to another element or so that a guiding element can guide the surgical instrument as planned) and can be further adjusted manually in order to reduce invasivity.

FIG. 6 shows an example of a display of an interface which places the guide elements one after another, each element being automatically placed (for example to stick to another element or so that a guiding element can guide the surgical instrument as planned) and can be further adjusted manually in order to reduce invasivity.

The interface displays a representation 210 of the anatomical structure and of each element intended to form part of the guide—in FIG. 6, one guiding element 130 comprising a cutting plane and two guiding elements 120 comprising a drilling hole are represented.

The shape (e.g. size in some directions, such as length, height, width), position, and/or orientation of some elements can be modified interactively.

Some modifications to the shape of some elements may be blocked or bounded (e.g. prevented from downsizing in order to ensure minimum stiffness of the guide, prevented from some rotations and translations of a guiding element in order to be consistent with planning).

The elements which propose no modification to the user are ideally automatically built with no interaction from the user, letting the user focus on the elements which he could modify.

At last, the guide is the addition of these elements.

In another preferred embodiment, the guide is defined as a parametric model, wherein its parameters define geometrical properties of its elements. Said geometrical properties may be typically height, length and depth of each block and junction element that will constitute the guide. Some parameters may be fixed, for example to prevent for too small thickness that might create weaknesses. Other parameters may be variable within a range to prevent from abnormal guides to be designed. Obviously, the guide will contain also some specific blocks that contain the contact elements and blocks that contain the guiding elements. But only the definition of the contact elements and the guiding elements is not sufficient to define entirely a guide. The parameters of the parametric model are then adjusted using geometrical rules that depend on data specific to the case. Said specific data may be landmarks defined on the anatomical structure, or landmarks defined on the implant once it is in the planned position. The selection of the parametric model and the rules for adjusting the parameters of the guide will constitute a particular choice of design. Multiple choices and design solutions are possible.

Then the guide can be manufactured by any suitable technique, such as stereolithography.

REFERENCES

WO 93/25157

The invention claimed is:

1. A method for constructing a patient-specific surgical guide comprising at least one contact element comprising a contact surface intended to match an anatomical structure to be treated and at least one guiding element for guiding a surgical instrument to treat said anatomical structure, said method comprising:
    receiving a 3D medical image of the anatomical structure of the patient;
    determining, in said 3D medical image, at least one region of interest containing a portion of the external surface of the anatomical structure intended to match a respective contact element of the surgical guide;
    segmenting the 3D medical image only in said determined region of interest so as to locally reconstruct the external surface of the anatomical structure;
    computing the contact surface of the contact element from said reconstructed external surface of the anatomical structure;
    constructing the at least one contact element to include the contact surface;
    defining the position of the at least one guiding element with respect to the anatomical structure;
    constructing the surgical guide by generating a rigid body including the at least one guiding element and said at least one contact element.

2. The method according to claim 1, wherein the determination of the at least one region of interest is carried out automatically.

3. The method according to claim 2, wherein the at least one determined region of interest is further adjusted interactively by a user.

4. The method according to claim 2, wherein the automatic determination of the at least one region of interest is based on anatomical landmarks.

5. The method according to claim 2, wherein the automatic determination of the at least one region of interest is based on a prior rough segmentation of the 3D medical image.

6. The method according to claim 1, wherein the determination of the at least one region of interest is carried out interactively.

7. The method according to claim 1, wherein at least two separate regions of interest are determined in the 3D image, each region of interest containing a portion of the external surface of the anatomical structure intended to match a respective contact element of the surgical guide.

8. The method according to claim 1, wherein the construction of the contact element comprises extruding a part of the rigid body until the computed contact surface.

9. The method according to claim 8, wherein the extrusion of said part of the rigid body is carried out by casting rays according to a selected direction towards the computed contact surface.

10. The method according to claim 9, wherein the contact surface is computed as an offset, by a determined distance along a direction opposite to the one of the rays, of the reconstructed local surface of the anatomical structure.

11. The method according to claim 9, wherein the computation of the contact surface comprises, for each ray intersecting the reconstructed local surface of the anatomical structure at an intersection point, raising each intersection point to the highest of its neighbors, the contact surface being defined by said raised points.

12. The method according to claim 1, wherein the contact surface is computed as being the reconstructed local surface of the anatomical structure.

13. The method according to claim 1, wherein the construction of the contact element comprises extruding a part of the rigid body toward the anatomical structure and subtracting the anatomical structure from said extruded part until the computed contact surface.

14. The method according to claim 1, comprising defining the guide as an addition of at least two elements, wherein at least one element has at least one determined degree of freedom with respect to the anatomical structure.

15. A computer program product comprising computer-readable instructions which, when loaded and executed on a suitable system, perform the following steps:
    receiving a 3D medical image of an anatomical structure of the patient;
    determining, in said 3D medical image, at least one region of interest containing a portion of the external surface of the anatomical structure intended to match a respective contact element of the surgical guide;
    segmenting the 3D medical image only in said determined region of interest so as to locally reconstruct the external surface of the anatomical structure;
    computing the contact surface of the contact element from said reconstructed external surface of the anatomical structure;
    constructing the at least one contact element to include the contact surface;
    defining the position of the at least one guiding element with respect to the anatomical structure;
    constructing the surgical guide by generating a rigid body including the at least one guiding element and said at least one contact element.

* * * * *